United States Patent [19]

Tanaka et al.

[11] Patent Number: 5,910,599
[45] Date of Patent: Jun. 8, 1999

[54] PREPARATION OF ANTIMONY ETHYLENEGLYOXIDE

[76] Inventors: Yoshio Tanaka, 19-17, Sujikai-Cho, Kishiwada-Shi, Osaka; Kazuyuki Koide; Hiroyuki Kawabata, both of 13-50, Juhachijo 1-Chome, Yodogawa-Ku, Osaka, all of Japan

[21] Appl. No.: 08/927,651

[22] Filed: Sep. 11, 1997

[30] Foreign Application Priority Data

Apr. 11, 1997 [JP] Japan ........................................ 110312

[51] Int. Cl.$^6$ ......................................................... C07F 9/90
[52] U.S. Cl. ............................................... 556/76; 556/64
[58] Field of Search .......................................... 556/64, 76

[56] References Cited

U.S. PATENT DOCUMENTS 3,054,760   9/1962   Worsley .
3,833,630   9/1974   Loeffler .

OTHER PUBLICATIONS

CA:122:95480, abs of "Determination of antimony in environmental samples", Anderson, J AOAC int, 77(6), pp. 1562–1568, 1994.

Chemical abs, vol. 63 abs No. 7875 a, abs of"Derivatives of antimony (III) with glycols", Mehrotra, J Indian Chem Soc. 42(5), pp. 327–332, Sep. 1965.

Chemical abs vol. 53 abs No. 7673h, abs of "Catalytic condensation of diglycol esters of dicarbocylic acids", Schouteden, Brit 805534, Apr. 1959.

Registry file on line nomenclature of Sb2(OCH2Ch2O)3 common names, Jun. 1998.

*Primary Examiner*—Gary Geist
*Assistant Examiner*—Jean F. Vollano

[57] ABSTRACT

The invention discloses a process of the preparation of antimony glycoloxide which comprises reacting an antimony halide with excess of ethylene glycol and further comprises the addition of a nitrogen compound selected from ammonia, organic amines and heterocyclic nitrogen rings.

3 Claims, No Drawings

PREPARATION OF ANTIMONY ETHYLENEGLYOXIDE

BACKGROUND OF THE INVENTION

This invention is concerned with a newly developed process for the production of antimony glycoloxide.

$$Sb_2(OCH_2CH_2O)_3$$

Antimony glycoloxide has been used as a catalyst in the polycondensation of dicarboxylic acids such as terephthalic acid and glycols such as ethylene glycol.

In the past there were two ways to produce a antimony glycoloxide. One is the reaction of antimony trioxide with an excess of ethylene glycol. And the other is the reaction of antimony tricarboxylates with at least a 1.5 molar excess of ethylene glycol. The former gives difficulties in obtaining the antimony glycoloxide in the high purity. And the latter is not an economical process to get said compound.

SUMMARY OF THE INVENTION

This invention provides a process for producing antimony glycoloxide by the reaction of halogenated antimony with excess ethylene glycol. In order to accelerate the reaction, it is preferable to add the amine. In such case the salt of halogenated hydrogen and amine will be formed. If enough ethylene glycol exists in the reaction mixture to dissolve the salt, the separation of antimony glycoloxide is very easy. The precipitation is filtered and then dryed under vacuum.

The halogenated antimony compounds useful in this invention can be listed as follows:
antimony trichloride, antimony tribromide, antimony triiodide, antimony trifluoride, antimony pentachloride, antimony pentabromide, antimony pentaiodide, antimony pentafluoride which are produced from the reaction of metallic antimony with a halogen directly.

Antimony glycoloxide is prepared by the reaction of halogenated antimony with ethylene glycol by scavenging the halogenated hydrogen. The reaction mixture should be free from the moisture by using an inert gas. The proportion of ethylene glycol against halogenated antimony should be preferable more than chemical equivalent.

In order to proceed the reaction of halogenated antimony with ethylene glycol, it is preferred to add nitrogen including organic chemicals which can scavenge the halogenated hydrogen and results in forming the aminium salt. Since aminium salt forming reaction is exothermic, it is prefered to cool the reaction vessel or before adding the nitrogen containing organic compound to the mixture, in order to avoid the abrupt reaction temperature raise, it is preferable that the nitrogen containing organic compounds should be dissolved with excess ethylene glycol.

Nitrogen containing organic compounds, which can scavenge the halogenated hydrogen and form the aminium salt, include various kind of amine compounds and ammonia. Some of them can be represented by the formula:

where N is nitrogen, $R_1$, $R_2$ and $R_3$ are each an aliphatic hydrocarbon, which carbon no. is 1–18, hydrogen or aromatic hydrocarbon. For example, methylamine, ethylamine, propylamine, n-octylamine, dimethylamine, diethylamine, dipropylamine, di-n-octylamine, trimethylamine, triethylamine, trioctylamine, tri-n-octylamine, aniline, N-methylaniline, diphenylamine, triphenylamine are included.

Further heterocyclic nitrogen containing organic compounds such as pyridine, piperidine and N-methylpyridine, and polyamine compounds such as ethylenediamine, hexamethylene diamine should be included.

When antimony glycoloxide is formed from halogenated antimony, ethylene glycol and nitrogen containing organic compound, it is preferable that enough ethylene glycol is existing in the reaction mixture to dissolve the formed aminium salt. If so, antimony glycoloxide is easily separable.

In order to understand well this invention, the following examples are described, but the invention should not be restricted to these examples:

EXAMPLE 1

45.6 g of antimony trichloride was added to 341 g of ethylene glycol. The mixture was heated to arround 40° C. under agitation. To this homogeneous transparent solution the mixture comprising of 60.8 g of triethylamine and 186 g of ethylene glycol was added. Immediately after the mixing of both solutions, the temperature of the liquid rose and a whitish precipitation was formed. After one night the solid was filtered by a Buchner funnel and then dried under vacuum. The weight of the product was 31.6 g and its antimony content was 57.26% (theoretical antimony content of antimony glycoloxide is 57.49%).

EXAMPLE 2

The reaction was repeated under the same conditions as those in Example 1 except that the reaction temperature was 90° C. The resultant precipitate was 29.6 g and its antimony content was 57.12%.

EXAMPLE 3

22.8 g of antimony trichloride was added to 155 g of ethylene glycol. The mixture was heated to arround 40° C. under agitation. To this homogeneous transparent solution, a mixture comprising of 21.9 g of diethylamine and 93 g of ethylene glycol was added. Immediately after mixing the temperature rose and a whitish precipitation was formed. After one night the solid was filtered and then dried under vacuum. 16.7 g of antimony glycoloxide, its antimony content was 57.25%, was obtained.

EXAMPLE 4

22.8 g of antimony trichloride was added to 155 g of ethylene glycol. The mixture was heated to arround 40° C. under agitation. To this homogeneous transparent solution, the mixture comprising of 23.7 g of pyridine and 93 g of ethylene glycol was added. Immediately after the mixing the temperature rose and a whitish precipitation was formed. After one night the solid was filtered and then dried under vacuum. 15.4 g of antimony glycoloxide, its antimony content was 57.82%, was obtained.

EXAMPLE 5

45.8 g of antimony tribromide was added to 155 g of ethylene glycol. The mixture was heated to arround 40° C. under agitation. To this homogeneous transparent solution, the mixture comprising of 30.4 g of triethylamine and 93 g of ethylene glycol was added. Immediately after mixing, the temperature rose and a whitish precipitation was formed. After one night the solid was filtered and dried under vacuum. 14.7 g of antimony glycoloxide, its antimony content was 57.74%. was obtained.

EXAMPLE 6

45.8 g of antimony trichloride was added to 124 g of ethlene glycol. The mixture was heated to arround 40° C. under agitation. To this homogeneous transparent solution, 60.6 g of triethyamine was added. The temperature of the mixture rose around 80–90° C. Immediately after mixing, a whitish precipitation was formed and 1–2 hrs later, the crystal was formed. After the analysis the precipitation was found to be antimony glycoloxide and the crystal was the salt of hydrogen chloride and triethylamine. In the cases of above mentioned example 1–5, the reaction mixture included enough ethylene glycol to dissolve the formed aminium salt of halogenated hydrogen, therefore only antimony glycoloxide was obtained. But in this case, since the added amount of ethyleneglycol was not enough to dissolve the formed aminium salt, the solid was a mixture of antimony glycoloxide and aminium salt, therefore another separation and purification were needed.

Comparative Example 1

The mixture comprising of 59.8 g of antimony triacetate, 31 g of ethylene glycol and 200 ml of ortho xylene was heated at 145° C. for 20 hours. After elimination of acetic acid formed, the solid was filtered and washed by ortho xylene and then dried at 90° C. for 3 hours. And finally 27 g of a whitish powder was obtained. From the analysis of antimony content, it was 80.5%, most of the product was found to be antimony trioxide.

We claim:

1. A process for the preparation of antimony glycoloxide which comprises forming a mixture by reacting either an antimony trihalide or an antimony pentahalide with ethylene glycol.

2. The process of claim 1 which further comprises adding a nitrogen compound selected from the group consisting of organic amines, polyamines, heterocyclic nitrogen containing compounds and ammonia, and additionally adding one or more molar equivalents of ethylene glycol, as compared to the initial moles of the antimony halide, to the mixture comprising the antimony halide and the ethylene glycol.

3. The process of claim 2 wherein the quantity of ethylene glycol is in a large enough excess to dissolve an aminium salt which forms during a reaction containing the nitrogen compound and a hydrogen halide by product.

* * * * *